United States Patent
Gunnarsson et al.

(10) Patent No.: US 12,254,404 B2
(45) Date of Patent: Mar. 18, 2025

(54) IMAGE REGISTRATION IN TREATMENT PLANNING

(71) Applicant: Elekta Ltd, Crawley (GB)

(72) Inventors: Niklas Gunnarsson, Stockholm (SE); Jens Sjölund, Sundbyberg (SE)

(73) Assignee: Elekta LTD., Crawley (GB)

( * ) Notice: Subject to any disclaimer, the term of this patent is extended or adjusted under 35 U.S.C. 154(b) by 340 days.

(21) Appl. No.: 17/182,572

(22) Filed: Feb. 23, 2021

(65) Prior Publication Data

US 2021/0268313 A1 Sep. 2, 2021

Related U.S. Application Data

(60) Provisional application No. 62/982,159, filed on Feb. 27, 2020.

(51) Int. Cl.
*G06N 3/08* (2023.01)
*G06T 7/246* (2017.01)
*G06T 7/73* (2017.01)
*A61N 5/10* (2006.01)

(52) U.S. Cl.
CPC ............... *G06N 3/08* (2013.01); *G06T 7/246* (2017.01); *G06T 7/73* (2017.01); *A61N 2005/1055* (2013.01); *G06T 2207/20081* (2013.01); *G06T 2207/20084* (2013.01)

(58) Field of Classification Search
None
See application file for complete search history.

(56) References Cited

U.S. PATENT DOCUMENTS

| | | | |
|---|---|---|---|
| 10,152,790 B2 * | 12/2018 | Han | G06T 7/0012 |
| 10,625,100 B2 * | 4/2020 | Berbeco | A61B 5/055 |
| 2020/0090371 A1 * | 3/2020 | Hu | H04N 7/183 |
| 2021/0158543 A1 * | 5/2021 | Sun | G16H 50/20 |

FOREIGN PATENT DOCUMENTS

WO WO-2017001920 A1 * 1/2017 ........... A61N 5/1049

OTHER PUBLICATIONS

Confidence propagation through CNNs for guided sparse depth regression, by Eldesokey et al., arXiv:1811.01791v2, Aug. 5, 2019 (Year: 2019).*
Generating patient specific pseudo-CT of the head from MR using atlas-based regression, BY Sjolund et al., 2015, Physicis in Medicine and Biology, Linkoping University post print (Year: 2015).*

* cited by examiner

*Primary Examiner* — Vikkram Bali
(74) *Attorney, Agent, or Firm* — Schwegman Lundberg & Woessner, P.A.

(57) ABSTRACT

The present invention relates to the field of radiation therapy and methods, software and systems for image registration. According to the present invention, methods for image registration of images of a patient comprising are provided. The method may include receiving a set of image data from the patient; selecting one or more tracking regions in the set of image data, each tracking region including a tracking point or set of tracking points; receiving sets of image data captured at different times from the patient; identifying corresponding tracking regions in the sets of image data captured at different times; estimating a displacement field describing displacement vectors for a number of points in the sets of image data including the tracking regions, each displacement vector specifying a position of a region in reference to a previous position.

18 Claims, 9 Drawing Sheets

IMAGE REGISTRATION IN TREATMENT PLANNING

CROSS REFERENCE TO RELATED APPLICATION

This application claims priority to U.S. Provisional Patent Application No. 62/982,159, filed Feb. 27, 2020, entitled Image Registration in Treatment Planning, the disclosure of which is incorporated by reference.

FIELD OF THE INVENTION

The present invention relates to the field of medical imaging and to systems, methods, computer-readable medium and modules for medical imaging in radiation therapy systems and in radiation therapy treatment.

BACKGROUND OF THE INVENTION

Radiotherapy is a therapy using ionizing radiation, often as part of cancer treatment where the intent is to control or kill malignant cells. One form of radiotherapy is brachytherapy, where a radiation source is placed inside or next to the area requiring treatment. Another form of radiotherapy is external beam radiotherapy, which employs a radiotherapy device that creates a radiation beam of particles (photons, electrons, protons and/or other ions) to irradiate a patient. One such radiotherapy device is a Gamma Knife, which irradiates a patient with a large number of low intensity gamma rays that emanate from radioactive sources and converge with high intensity and high precision at a target (e.g., a tumor). External beam radiotherapy also includes linear particle accelerator (linac)-based radiotherapy (e.g., 3D-CRT, IMRT, VMAT) and circular particle accelerators (e.g., cyclotron, synchrotron, and synchrocyclotron).

A linear accelerator uses radio-frequency energy to create a varying magnetic and electrical field in an elongated accelerating chamber—hence a "linear" accelerator. Electrons are fed into the chamber and are accelerated to near light speed. The resulting beam can be used directly as a form of radiation, but it is more usual to direct this to a suitable "target", a block of an appropriate heavy metal such as tungsten. The electron beam impinges on the tungsten block and causes it to emit a beam of x-radiation. The geometry of the electron beam and the tungsten surface are arranged so that the x-ray beam departs perpendicular to the incoming electron beam and can thus be directed towards a patient.

The x-ray beam is collimated to a suitable shape and passes through the patient causing tissue damage. By suitable collimation and by moving the linear accelerator around the patient so that it approaches from a range of directions, such systems can minimize the dosage outside the tumor and maximize it within the tumor. One such radiation device is Elekta Unity®. The Elekta Unity® provides real-time visualization during the treatment using MRI (Magnetic Resonance Imaging) scanners (and/or CT (Computed Tomography) scanners). This offers, for example, real-time adaptive planning for fast dose shaping. Accordingly, fast and accurate image registration of the medical images are necessary. In medical imaging, image registration is used to relate multiple images of the same anatomical region to each other. It already plays an important role for adaptive radiotherapy, where a fractionated treatment scheme may be adapted based on re-scans but is too slow for real-time applications.

Image registration is often formulated as an optimization problem that is solved iteratively. The objective is to find a "plausible" deformation field that e.g. maximizes the image similarity of the fixed and the moving images or minimizes the average distance between corresponding landmarks in the two images (so called landmark-based registration).

Accurate registration of soft tissue often requires non-rigid registration methods, which can be categorized as either parametric or non-parametric. Non-parametric methods estimate the deformation at every position in the image, while parametric methods use a lower-dimensional representation of the deformation field. Because of the lower dimensionality, parametric methods are faster than non-parametric ones.

Examples of parametric representations include thin plate splines, B-splines or other kernel regression models. Kernel regression models represent the local deformation as a weighted sum of the deformations at a set of predefined control points. The weight is determined by a kernel function (radial basis function) that depends on the distance between two points. Thin plate splines correspond to a choice of basis with global support, while B-splines have local support. Revaud et al. (Revaud, Jerome, et al. "Epicflow: Edge-preserving interpolation of correspondences for optical flow." Proceedings of the IEEE conference on computer vision and pattern recognition, 2015) proposed to estimate the optical flow, which is essentially the deformation field, by combining a neural network for sparse patch matching (described in Weinzaepfel, Philippe, et al. "DeepFlow: Large displacement optical flow with deep matching." *Proceedings of the IEEE international conference on computer vision,* 2013) and a sparse-to-dense interpolation scheme. Two sparse-to-dense interpolation schemes were proposed: kernel regression (also known as Nadaraya-Watson estimation) and locally-weighted affine estimation. In both cases the distance was not the Euclidean distance, but the geodesic distance in an edge aware feature map.

However, these prior art methods are too slow for real-time applications and demands of modern radiation therapy systems such as Elekta Unity® which include MRI scanners. Another issue is that most machine learning methods are trained to work for a particular type of image, while MRI scanners often use a wide range of image contrasts.

SUMMARY OF THE INVENTION

An object of the present invention is to provide more efficient and improved methods, systems, modules and computer-readable medium for image registration of images in radiation therapy systems and in radiation therapy treatment.

Another object of the present invention is to provide methods, systems, modules and computer-readable medium for image registration of MRI images capable of handling a wide range of image contrast.

A further object of the present invention is to provide methods, systems, modules and computer-readable medium for image registration in real-time applications.

In the context of the present invention, the term "feature" or "features" relates to the information on which decisions are made, e.g. edges in the image. In many cases the features will be in the form of an image (feature map). This is aligned with
https://en.wikipedia.org/wiki/Feature extraction,
where it says that "feature extraction starts from an initial set of measured data and builds derived values (features) intended to be informative and non-redundant, facilitating the subsequent learning and generalization steps, and in some cases leading to better human interpretations."

Further, in the context of the present invention, the term "tracking target" or "tracking targets" relates to the points, lines or other shapes (e.g. a banana-shaped region) that are desired to find correspondences for. Could also be an image with continuous values, e.g. between 0 and 1. A tracking target is the desired output when training a discriminative correlation filter (DCF), where it is normally chosen as a sharply peaked Gaussian.

In the context of the present invention, the term "tracking region" relates to the region (in position space) from which features are derived/retrieved to predict whether a tracking target is matched. For a DCF trained on a given tracking target, the tracking region is the neighborhood of the tracking target on which the filter acts.

Moreover, in the context of the present invention, the term "search region" relates to the region where the search for matching tracking targets is performed. The search region could be the whole image (feature) but could be made smaller to reduce computations.

The present invention is based on a combination of a feature tracker with a sparse-to-dense interpolation scheme. A fixed number of features are tracked and the displacement field or motion field for each tracking region is calculated. To estimate the dense displacement field a sparse-to-dense interpolation method is used. In preferred embodiments, the feature tracker uses a discriminative correlation filter (Daneilljan, Martin et al "ECO: Efficient Convolution Operators for Tracking". *Proceeding if the IEEE Conference on Computer Vision and Pattern Recognition,* 2017) and the sparse-to-dense interpolation uses normalized convolutions (Eldesokey, Abdelrahman et al "Confidence Propagation through CNNs for Guided Sparse Depth Regression". *IEEE Transactions of Pattern Analysis and Machine Learning,* 2019). By using a discriminate correlation filter as tracking algorithm, a modality agnostic model is created. In the interpolation, a trainable deep learning method using normalized convolutions with constant basis functions, where weights for the basis are trained, is utilized.

According to an aspect of the present invention, there is provided a method for image registration of images of a patient. The method comprises receiving a set of image data from the patient and selecting one or more tracking regions in the set of image data, each tracking region including a tracking target or set of tracking targets. Further, sets of image data captured at different times from the patient are received and corresponding tracking targets in the sets of image data captured at different times are identified. Moreover, a displacement field describing displacement vectors for a number of points in the sets of image data including the tracking regions is estimated, each displacement vector specifying a position of a point in reference to a previous position.

According to a second aspect of the present invention, there is provided a computer-readable medium having stored therein computer-readable instructions for a processor, wherein the instructions when read and implemented by the processor, cause the processor to: select one or more tracking regions in a set of image data of an image of a patient, each tracking region including a tracking target or set of tracking targets; identify corresponding tracking targets in sets of image data from images captured at different times of the patient; estimate a displacement field describing displacement vectors for a number of points in the sets of image data including the tracking regions, each displacement vector specifying a position of a point in reference to a previous position.

According to a further aspect of the present invention, there is provided a method for training a machine learning model to be used in image registration of images of a patient comprising: gathering training data to the machine learning model; estimating a loss function and/or its gradient of the machine learning model using the training data; and updating parameters of a parameterized model of the machine learning model based on estimated loss function and/or its gradient.

In embodiments of the present invention, a sparse field describing motion vectors of the tracking targets specifying a position of a tracking target in reference to a previous position is created.

In embodiments of the present invention, a representation of an image based on the displacement field is created.

In embodiments of the present invention, the step of selecting tracking regions includes a feature extraction, wherein the tracking regions are selected based on feature extraction.

In embodiments of the present invention, the step of selecting a number of regions in the set of image data, each region including a tracking target or set of tracking targets comprises adding or removing at least one tracking region as a response to a performance of the selected tracking region and/or as an update of a feature extraction.

In embodiments of the present invention, it is determined whether the selected tracking regions deliver a satisfying performance, and if it is determined that the performance is satisfactory, terminating the selection of tracking regions; and if it is determined that the performance is not satisfactory, adding or removing tracking targets.

In embodiments of the present invention, the step of identifying corresponding tracking targets in the sets of image data from the images, further comprises identifying corresponding potential tracking targets using a feature extracting model; identifying matching candidates for the potential tracking targets; and using the matching candidates in estimating a displacement field.

In embodiments of the present invention, the step of identifying corresponding tracking regions in the sets of image data from the images, further comprises using identified tracking regions for training the feature extraction model and for updating the feature extracting model.

In embodiments of the present invention, the step of estimating a displacement field describing displacement vectors includes using interpolation of the tracking results to estimate the displacement field.

In embodiments of the present invention, the step of estimating further comprises using image data from the received sets of image data in the interpolation.

In embodiments of the present invention, the step of estimating further comprises using a machine learning model to estimate the displacement field, wherein the sparse field is used as input.

In embodiments of the present invention, the machine learning model is a deep learning model. For example, the deep learning model uses normalized convolutions. In embodiments of the present invention, the machine learning model is a neural network.

In embodiments of the present invention, the parameterized model of the machine learning model is specified; and the loss function and of the machine learning model is specified.

In embodiments of the present invention, synthetic image data is generated to the machine learning model for use as training data.

In embodiments of the present invention, basic displacement fields describing displacement vectors for a number of points in a data set, each displacement vector specifying a position of a point in reference to a previous position, are created; the positions are sampled; and displacement fields at sampled positions are estimated as input training data.

In embodiments of the present invention, image data of a patient is gathered, the displacement field is applied to the image data to create a resulting displacement filed, and the input training data is modified based on the resulting displacement field.

In embodiments of the present invention, further training data to the machine learning model is gathered if a convergence criterion has not been met and the loss function and/or its gradient of the machine learning model is estimated, the training data is used, and parameters of a parameterized model of the machine learning model is updated based on the estimated loss function and/or its gradient.

As the skilled person realizes, steps of the methods according to the present invention, as well as preferred embodiments thereof, are suitable to realize as computer program or as a computer readable medium.

Further objects and advantages of the present invention will be discussed below by means of exemplifying embodiments.

DETAILED DESCRIPTION OF THE DRAWINGS

Figure 1:
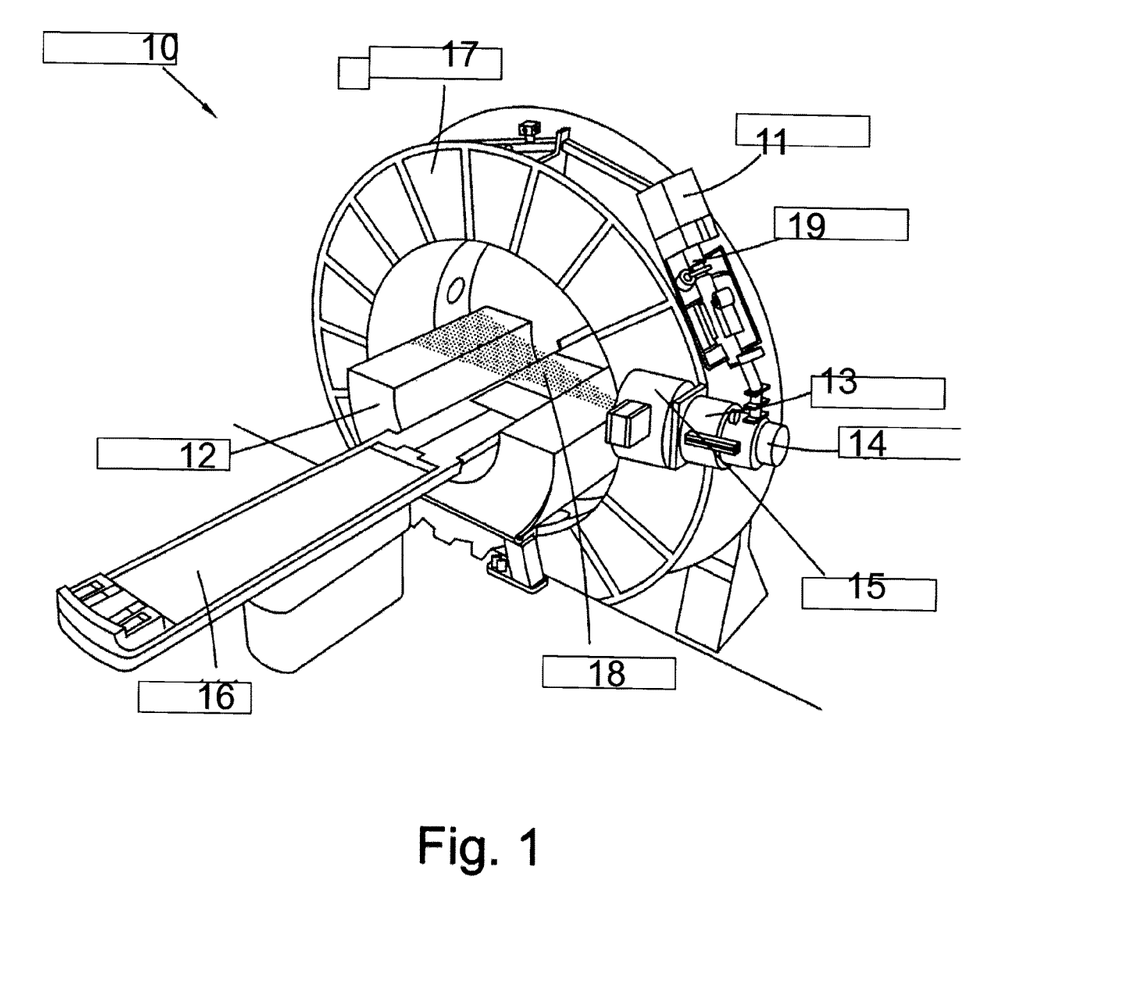
FIG. 1 shows a radiation therapy device in which the present invention can be used.

The present invention is preferably implemented in a device for treating a patient with ionising radiation. FIG. 1 depicts a radiotherapy device suitable for delivering, and configured to deliver, a beam of radiation to a patient during radiotherapy treatment. The device and its constituent components will be described generally for the purpose of providing useful accompanying information for the present invention. The device depicted in FIG. 1 is in accordance with the present disclosure and is suitable for use with the disclosed systems and apparatuses. While the device in FIG. 1 is an MR-linac, the implementations of the present disclosure may be any radiotherapy device, for example a linac device.

The device 10 depicted in FIG. 1 is an MR-linac. The device 10 comprises both MR imaging apparatus 12 and radiotherapy (RT) apparatus which may comprise a linac device. The MR imaging apparatus 12 is shown in cross-section in the diagram. In operation, the MR scanner produces MR images of the patient, and the linac device produces and shapes a beam of radiation and directs it toward a target region within a patient's body in accordance with a radiotherapy treatment plan. The depicted device does not have the usual 'housing' which would cover the MR imaging apparatus 12 and RT apparatus in a commercial setting such as a hospital.

The MR-linac device depicted in FIG. 1 comprises a source of radiofrequency waves 11, a waveguide 13, a source of electrons 14, a source of radiation 14, a collimator 15 such as a multi-leaf collimator configured to collimate and shape the beam, MR imaging apparatus 12, and a patient support surface 16. In use, the device would also comprise a housing (not shown) which, together with the ring-shaped gantry, defines a bore. The moveable support surface 16 can be used to move a patient, or other subject, into the bore when an MR scan and/or when radiotherapy is to commence. The MR imaging apparatus 112, RT apparatus, and a subject support surface actuator are communicatively coupled to a controller or processor. The controller is also communicatively coupled to a memory device comprising computer-executable instructions which may be executed by the controller.

The RT apparatus comprises a source of radiation and a radiation detector (not shown). Typically, the radiation detector is positioned diametrically opposed to the radiation source. The radiation detector is suitable for, and configured to, produce radiation intensity data. In particular, the radiation detector is positioned and configured to detect the intensity of radiation which has passed through the subject. The radiation detector may also be described as radiation detecting means, and may form part of a portal imaging system.

The radiation source may comprise a beam generation system. For a linac, the beam generation system may comprise a source of RF energy 11, an electron gun 14, and a waveguide 13. The radiation source is attached to the rotatable gantry 17 so as to rotate with the gantry 17. In this way, the radiation source is rotatable around the patient so that the treatment beam 18 can be applied from different angles around the gantry 17. In a preferred implementation, the gantry is continuously rotatable. In other words, the gantry can be rotated by 360 degrees around the patient, and in fact can continue to be rotated past 360 degrees. The gantry may be ring-shaped. In other words, the gantry may be a ring-gantry.

The source 11 of radiofrequency waves, such as a magnetron, is configured to produce radiofrequency waves. The source 11 of radiofrequency waves is coupled to the waveguide 13 via circulator 19, and is configured to pulse radiofrequency waves into the waveguide 13. Radiofrequency waves may pass from the source 11 of radiofrequency waves through an RF input window and into an RF input connecting pipe or tube. A source of electrons 14, such as an electron gun, is also coupled to the waveguide 13 and is configured to inject electrons into the waveguide 13. In the electron gun 14, electrons are thermionically emitted from a cathode filament as the filament is heated. The temperature of the filament controls the number of electrons injected. The injection of electrons into the waveguide 13 is synchronised with the pumping of the radiofrequency waves into the waveguide 13. The design and operation of the radiofrequency wave source 11, electron source and the waveguide 13 is such that the radiofrequency waves accelerate the electrons to very high energies as the electrons propagate through the waveguide 13.

The design of the waveguide 13 depends on whether the linac accelerates the electrons using a standing wave or travelling wave, though the waveguide typically comprises a series of cells or cavities, each cavity connected by a hole or 'iris' through which the electron beam may pass. The cavities are coupled in order that a suitable electric field pattern is produced which accelerates electrons propagating through the waveguide 13. As the electrons are accelerated in the waveguide 13, the electron beam path is controlled by a suitable arrangement of steering magnets, or steering coils, which surround the waveguide 13. The arrangement of steering magnets may comprise, for example, two sets of quadrupole magnets.

Once the electrons have been accelerated, they may pass into a flight tube. The flight tube may be connected to the waveguide by a connecting tube. This connecting tube or connecting structure may be called a drift tube. The electrons travel toward a heavy metal target which may comprise, for example, tungsten. Whilst the electrons travel through the flight tube, an arrangement of focusing magnets act to direct and focus the beam on the target.

To ensure that propagation of the electrons is not impeded as the electron beam travels toward the target, the waveguide 13 is evacuated using a vacuum system comprising a vacuum pump or an arrangement of vacuum pumps. The pump system is capable of producing ultra-high vacuum (UHV) conditions in the waveguide 13 and in the flight tube. The vacuum system also ensures UHV conditions in the electron gun. Electrons can be accelerated to speeds approaching the speed of light in the evacuated waveguide 13.

The source of radiation is configured to direct a beam 18 of therapeutic radiation toward a patient positioned on the patient support surface 16. The source of radiation may comprise a heavy metal target toward which the high energy electrons exiting the waveguide are directed. When the electrons strike the target, X-rays are produced in a variety of directions. A primary collimator may block X-rays travelling in certain directions and pass only forward travelling X-rays to produce a treatment beam 18. The X-rays may be filtered and may pass through one or more ion chambers for dose measuring. The beam can be shaped in various ways by beam-shaping apparatus, for example by using a multi-leaf collimator 15, before it passes into the patient as part of radiotherapy treatment.

In some implementations, the source of radiation is configured to emit either an X-ray beam or an electron particle beam. Such implementations allow the device to provide electron beam therapy, i.e. a type of external beam therapy where electrons, rather than X-rays, are directed toward the target region. It is possible to 'swap' between a first mode in which X-rays are emitted and a second mode in which electrons are emitted by adjusting the components of the linac. In essence, it is possible to swap between the first and second mode by moving the heavy metal target in or out of the electron beam path and replacing it with a so-called 'electron window'. The electron window is substantially transparent to electrons and allows electrons to exit the flight tube.

The subject or patient support surface 16 is configured to move between a first position substantially outside the bore, and a second position substantially inside the bore. In the first position, a patient or subject can mount the patient support surface. The support surface 16, and patient, can then be moved inside the bore, to the second position, in order for the patient to be imaged by the MR imaging apparatus 12 and/or imaged or treated using the RT apparatus. The movement of the patient support surface is effected and controlled by a subject support surface actuator, which may be described as an actuation mechanism. The actuation mechanism is configured to move the subject support surface in a direction parallel to, and defined by, the central axis of the bore. The terms subject and patient are used interchangeably herein such that the subject support surface can also be described as a patient support surface. The subject support surface may also be referred to as a moveable or adjustable couch or table.

The radiotherapy apparatus/device depicted in FIG. 1 also comprises MR imaging apparatus 12. The MR imaging apparatus 12 is configured to obtain images of a subject positioned, i.e. located, on the subject support surface 16. The MR imaging apparatus 12 may also be referred to as the MR imager. The MR imaging apparatus 12 may be a conventional MR imaging apparatus operating in a known manner to obtain MR data, for example MR images. The skilled person will appreciate that such a MR imaging apparatus 12 may comprise a primary magnet, one or more gradient coils, one or more receive coils, and an RF pulse applicator. The operation of the MR imaging apparatus is controlled by the controller.

The controller is a computer, processor, or other processing apparatus. The controller may be formed by several discrete processors; for example, the controller may comprise an MR imaging apparatus processor, which controls the MR imaging apparatus 18; an RT apparatus processor, which controls the operation of the RT apparatus; and a subject support surface processor which controls the operation and actuation of the subject support surface. The controller is communicatively coupled to a memory, e.g. a computer readable medium.

The linac device also comprises several other components and systems as will be understood by the skilled person. For example, in order to ensure the linac does not leak radiation, appropriate shielding is also provided.

Figure 2:
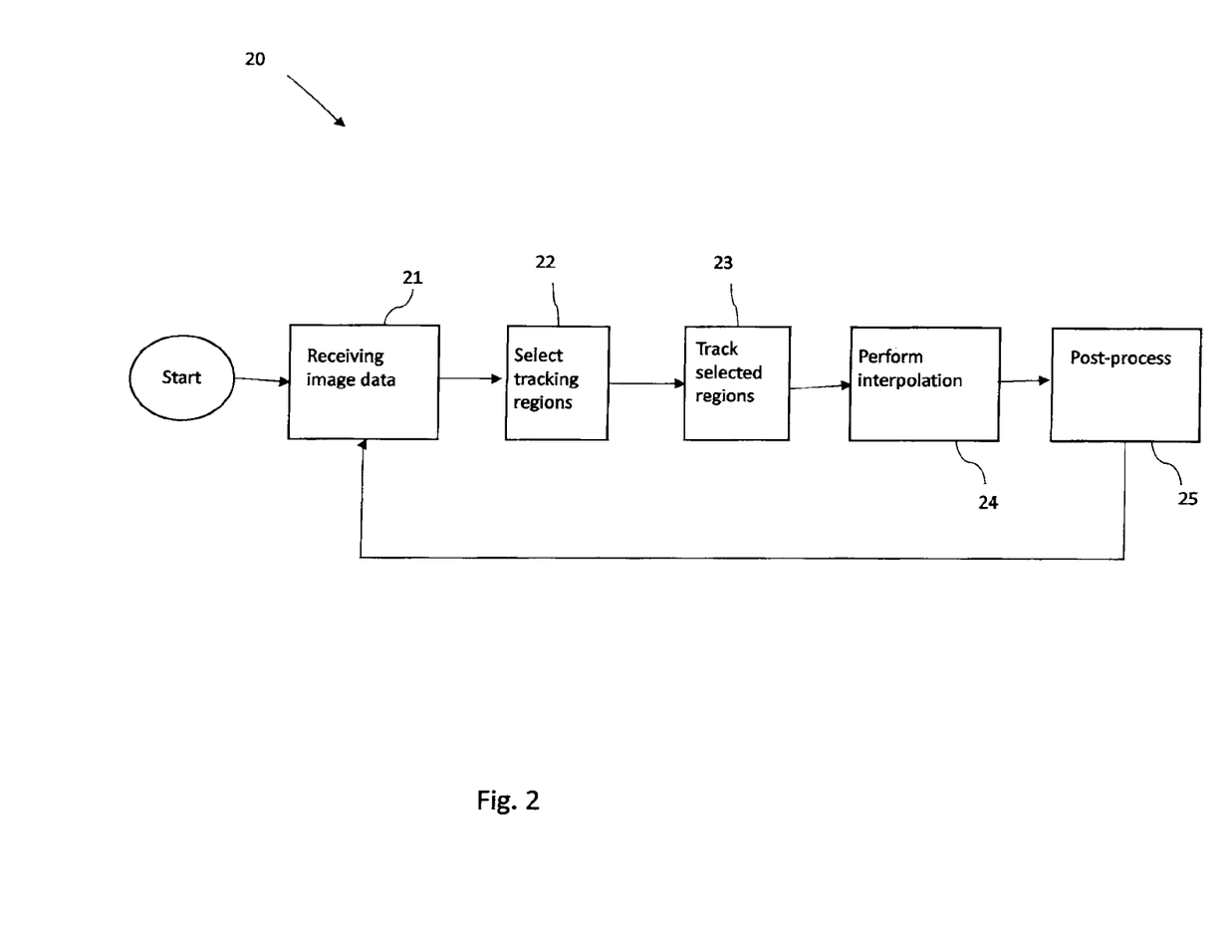
FIG. 2 is a flow chart illustrating an embodiment of the present invention.

With reference now to FIG. 2, a general method 20 according to the present invention will be described. At step 21, sets of medical image data are received, for example, a stream of medical images of a patient including a target to be treated with radiation therapy. A pre-processing step can be implemented, for example, some form of dimensionality reduction such as PCA, t-SNE, autoencoder; or some classical computer vision method, e.g. resizing, de-texturize, de-colorize, edge enhancement, salient edge map, local phase, flip, rotate, crop, image registration; or some machine learning method, e.g. a convolutional neural network. Further, it may be some classical preprocessing method for that medical imaging modality: bias-field correction, intensity normalization, distortion correction, denoising.

Figure 3:
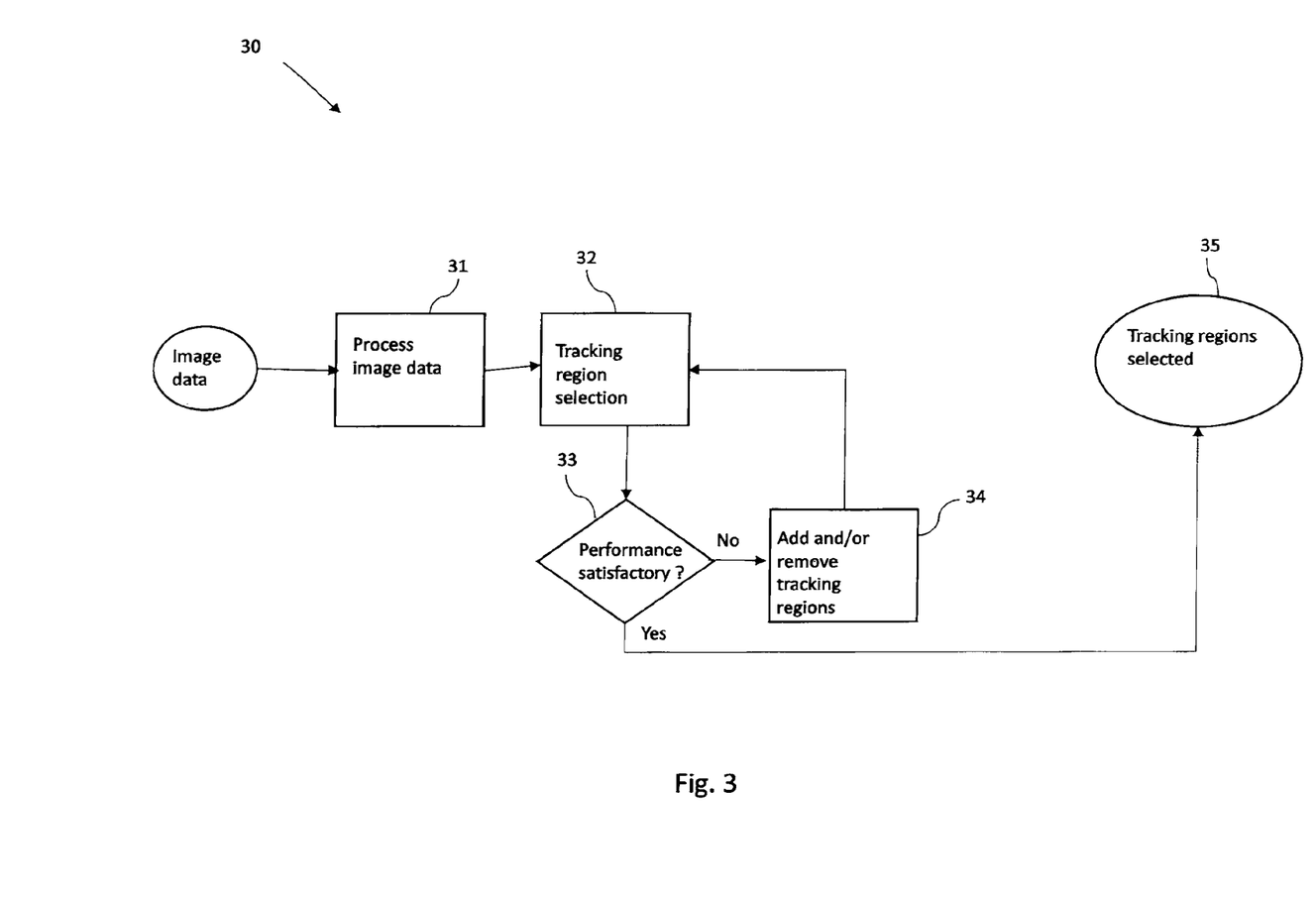
FIG. 3 is a flow chart illustrating an embodiment of the present invention.

In step 22, tracking regions in an image are selected. The selection of regions may be based on a distance based procedure, a segmentation mask procedure, an edge-based procedure, a superpixel procedure, a good features to track procedure, a randomized procedure, or a gridded procedure. In FIG. 3, the tracking region selection 30 is described in more detail. A pre-process is performed in step 31, in step 32 the tracking region selection is started. Preferably, a first set of tracking regions is selected. In step 33, it is checked whether the performance is satisfactory or not. If yes, that is the selected set of tracking regions fulfil predetermined conditions, for example, no outliers found in the set, the selected regions are not too many, a score is above a predetermined level, the procedure proceeds to step 35 where the selection of tracking regions is terminated. On the other hand, if not, then in step 33, the procedure proceeds to step 34 where regions are removed and/or added. For example, regions are removed if they have a low score, are considered as outliers by joint estimation, there are too many regions according to a predetermined criteria, or if the method is running too slow. Regions are added when: estimates are too noisy, too low score, or score maps are not sharply peaked (in which one may sample new regions based on the score).

In step 23, the tracking of selected tracking regions is initiated, for example, using a feature extractor. For example, a discriminative correlation filter that optimizes a correlation filter for a given region may be used. By using a discriminate correlation filter as tracking algorithm, a modality agnostic model can be created. Since the filter is trained and learn from its initial image and it's updated online no modality assumptions have to be made. Other choices of tracking methods are of course possible, e.g. the more traditional Lucas-Kanade (1981) method. The tracking may use old images, or intermediate results (e.g. confidence maps) and/or vector fields as additional inputs. Update of the feature extractor can be done at fixed interval or dynamically (when some criteria is met), in either case it need not happen on every iteration. In the preferred embodiment, the feature extractor is a discriminative correlation filter (DCF), e.g. MOSSE, ECO, C-COT, DiMP, ATOM, but other types of correlation/convolution filters are also possible as well as different kinds of handcrafted feature transforms SIFT, RIFT, G-RIF, SURF, GLOH, HOG. Joint estimation could use information from external sources such as ultrasound, respirometry, surface tracking, planar X-ray, CT, 1D MRI, 2D MRI, 3D MRI, camera. Joint estimation could use some form of regularization that could, for example, be handcrafted, a statistical prior, or a learned regularization. The feature extractor could be updated based on the result of joint estimation.

Figure 4:
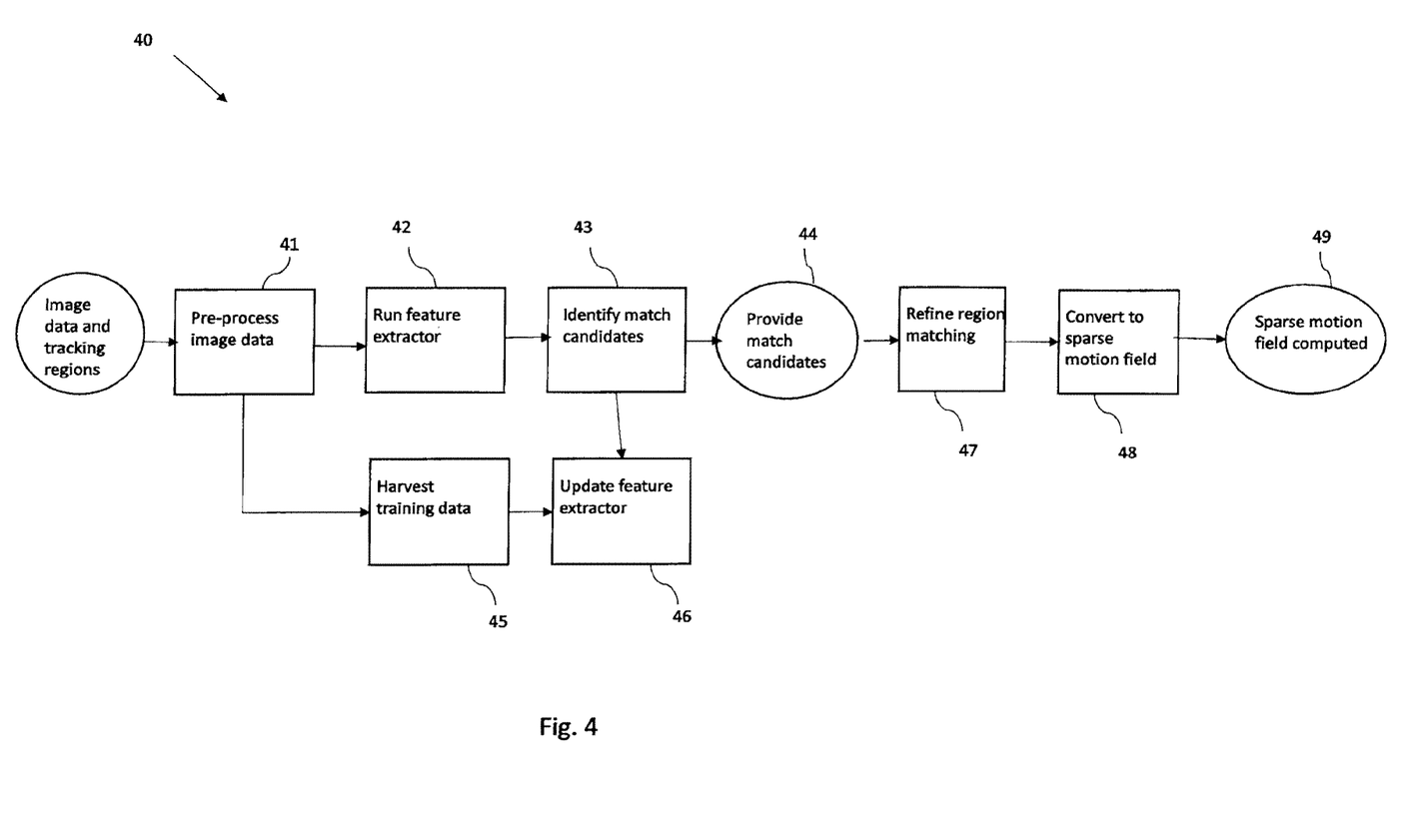
FIG. 4 is a flow chart illustrating an embodiment of the present invention.
Figure 5:
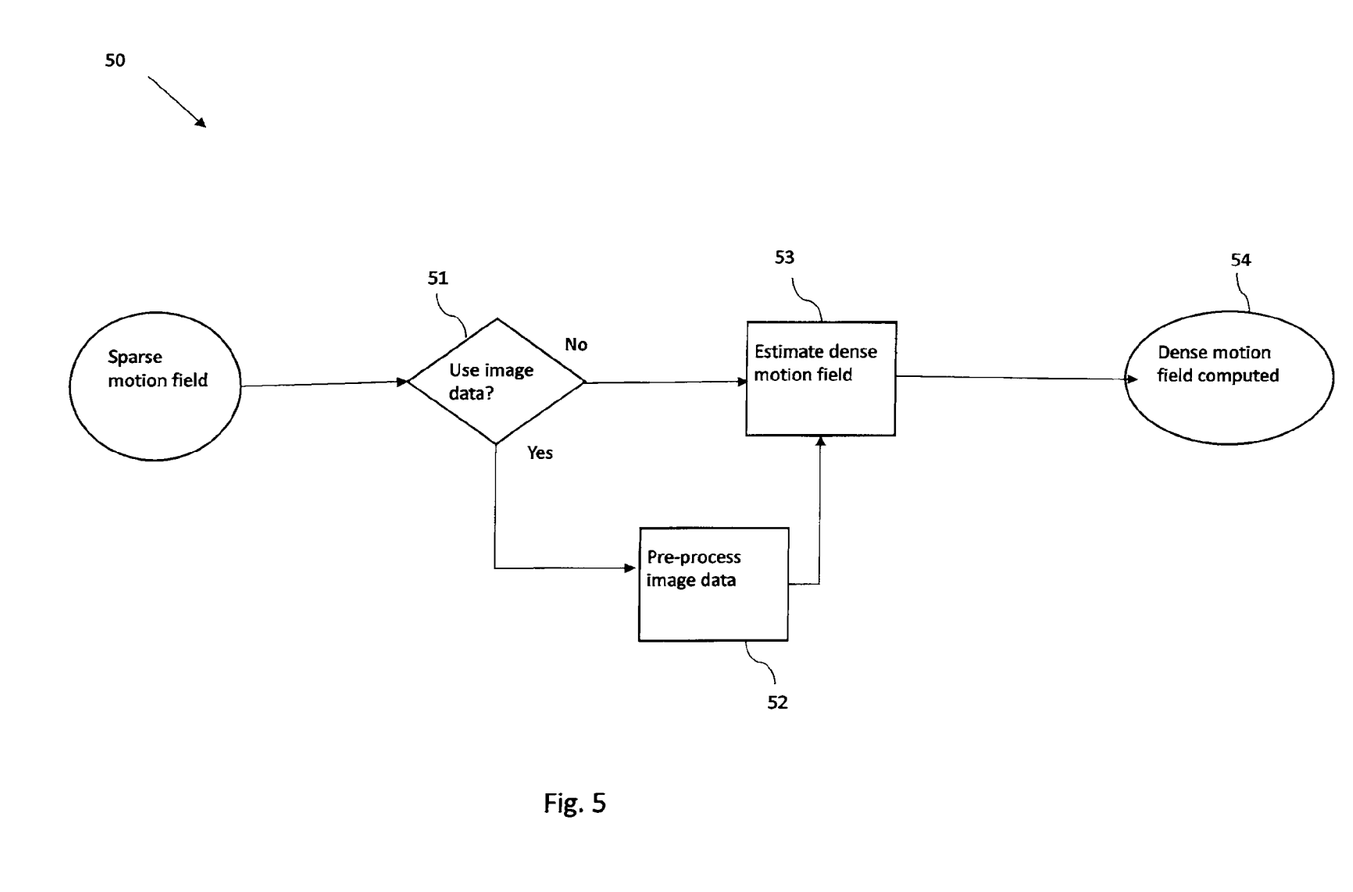
FIG. 5 is a flow chart illustrating an embodiment of the present invention.

In FIG. 4, the tracking procedure 40 is described in more detail. In step 41, a pre-processing of image data captured at one instant or from several different times is performed. In step 42, the feature extractor is run to extract matching tracking targets in consecutive images. In step 44, matching candidates are provided. The pre-processed image data is also used as training data for the feature extractor in step 45, as mentioned above, and to update the feature extractor in step 46. A refining process of the matching candidates may be performed in step 47 and in step 48, a conversion to a sparse motion field is performed and in step 49 the sparse motion field is computed. In a preferred embodiment, the feature tracker uses a discriminative correlation filter (Daneilljan, Martin et al "ECO: Efficient Convolution Operators for Tracking". *Proceeding if the IEEE Conference on Computer Vision and Pattern Recogintion,* 2017).

Returning now to FIG. 2, the procedure continues to step 24 where the interpolation is performed. With reference to FIG. 4, the interpolation is described in more detail. The sparse motion field is input in the interpolation. In step 51, it is checked whether image data is also to be used in the interpolation. If no, in step 51, the procedure proceeds to step 53 where a dense motion field or displacement field is estimated, and in step 54 the dense motion field is computed. On the other hand, if image data is also to be used, the procedure proceeds to step 52, where the image data is pre-processed and then forwarded to step 53, where the estimation of the dense motion field is performed.

As mentioned above, the interpolation is performed using normalized convolution. The confidence could be binary (1 if tracked, 0 otherwise), or at same locations but real-valued (preferably a value between, or equal to, 0 and 1). Further, it is also possible to use predictions from previous iterations as a prior. Normalized convolution is an example from a more general class of filtering methods, referred to as moving least-squares (Milanfar 2013) although it is known under other names as well. Mathematically, it's a class of non-parametric estimators where the value of an underlying signal z(x) at position x is estimated from the weighted least-squares problem:

$$\hat{z}(x_j) = \arg\min_{z(x_j)} \Sigma_{i=1}^{n} (y_i - z(x_i))^2 K(x_i, x_j, y_i, y_j).$$

Where the kernel (weight) K is a non-negative, unimodal function that is symmetric with respect to i and j. K measures the "similarity" between the samples $y_i$ and $y_j$, at respective positions $x_i$ and $x_j$. If the kernel function is restricted to be only a function of the spatial locations $x_i$ and $x_j$, then the resulting formulation is what is known as (classical, or not data-adaptive) kernel regression in the nonparametric statistics literature. Perhaps more importantly, the key difference between local and nonlocal patch-based methods lies essentially in the definition of the range, n, of the sum above. Specifically, indices covering a small spatial region around a pixel of interest define local methods, and vice versa.

The interpolation step could use a (finite-dimensional) parameterized representation or an infinite-dimensional representation. Results could be predicted directly or could be found by an iterative optimization algorithm. Most conventional optimization methods would apply to the parameterized case while the infinite-dimensional case could be approached using e.g. a variational framework (solving the Euler-Lagrange equation). The interpolation could use any scattered interpolation method, for instance nearest-neighbor interpolation, triangulated irregular network-based natural neighbor, triangulated irregular network-based linear interpolation (a type of piecewise linear function), inverse distance weighting, kriging, gradient-enhanced kriging (GEK), thin plate spline, polyharmonic spline (the thinplate-spline is a special case of a polyharmonic spline), radial basis function (polyharmonic splines are a special case of radial basis functions with low degree polynomial terms), least-squares spline, or natural neighbor interpolation.

Figure 6:
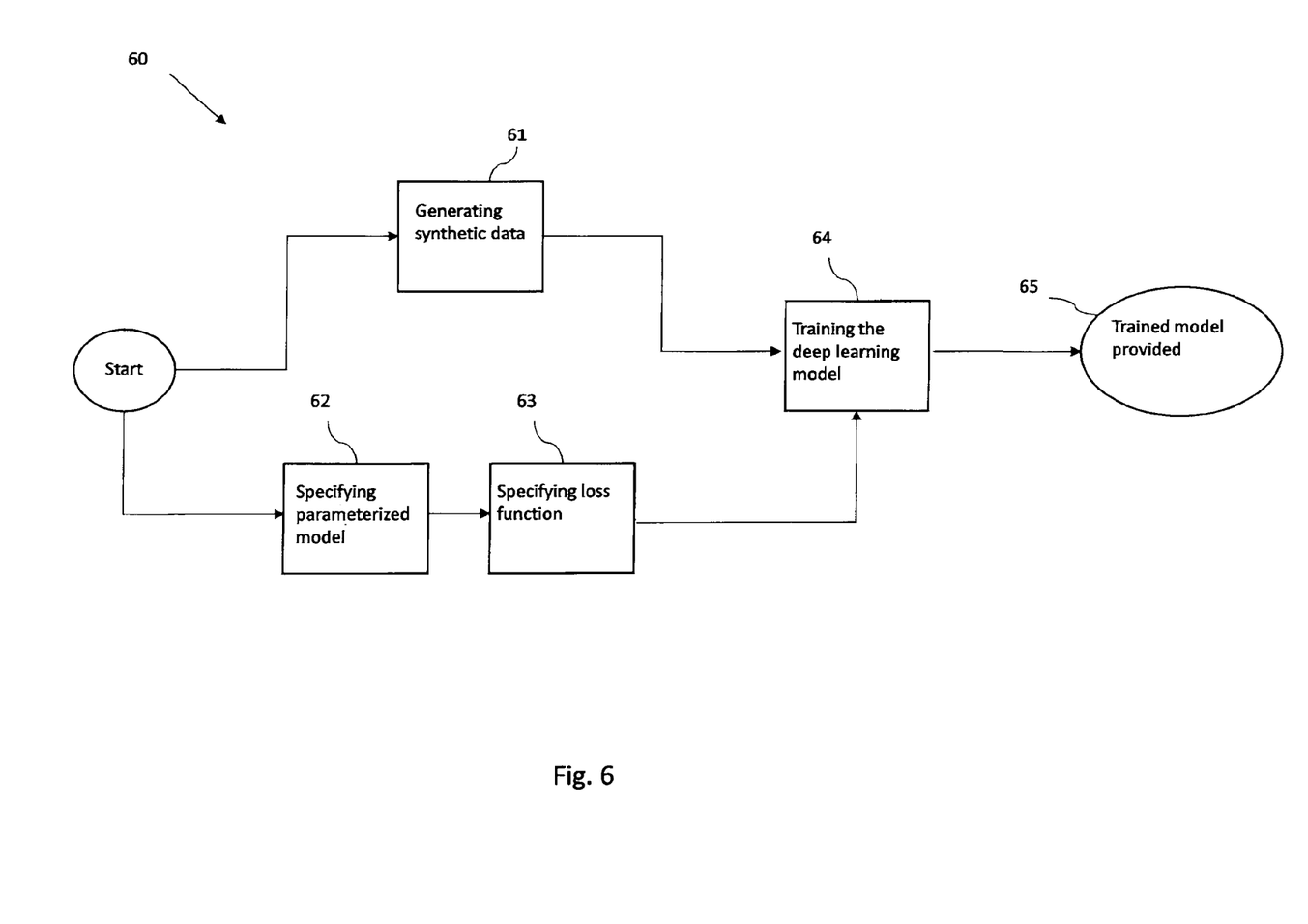
FIG. 6 is a flow chart illustrating an embodiment of the present invention.

With reference now to FIG. 6, a training phase in accordance with the present invention will be described. In accordance with the present invention, a trainable deep learning method using normalized convolutions with constant basis functions is preferably used in the interpolation step as mentioned above. Normalized convolutions extend ordinary convolutions by using a confidence map to improve interpolation of irregularly sampled and/or noisy data. The architecture of the network uses a coarse-to-fine schema which down-sample the features to lower resolutions and propagates the result by up-sampling and concatenating with the finer resolution. Inputs to the network is the sparse displacement field and the confidence map. The network uses a coarse-to-fine schema and down-sample the features using max-pooling based on the confidence feature map.

In the training of the deep learning model, deformation fields or displacements fields are synthesized, giving the deformation sampled at a set of sparse and irregular locations as input, and asking the deep learning model to estimate the dense deformation field. Since most physiological deformations are diffeomorphic, such deformations are synthesized using a geodesic shooting method. The sampling points can, for example, be selected using a randomized procedure. As a pre-processing step in the training procedure, noise can also be added to the synthetic displacement field which are reflected in the confidence map. When estimating the dense deformation field, the uncertainty from the discriminative correlation filter can be used in the confidence map during the interpolation.

In step 61, synthetic image data is gathered or generated. In step 62, a parameterized model for the deep learning model is created or specified and in step 63, a loss function is created or specified. The loss function can be based on the motion field or image similarity, or some property derived from those. Examples include End-point error (EPE), mean-squared error, Huber norm, normalized cross-correlation, mutual information, SSIM, accuracy of propagated segmentation maps ((soft) Dice, cross-entropy). The loss function could itself be part of the training, as in adversarial training.

In step 64, the deep learning model is trained and in step 65 a trained model is provided. In the preferred embodiment the machine learning algorithm is based on supervising learning, but it would be possibly to use any method in the spectrum from supervised to unsupervised learning. This includes semi-supervised learning, weakly supervised learning, transfer learning, adversarial learning, multi-task learning, domain adaptation, meta-learning. It could use reinforcement learning to e.g. select neural network architecture or, more generally, to combine, mix, rearrange the pipeline and its constituents.

Figure 7:
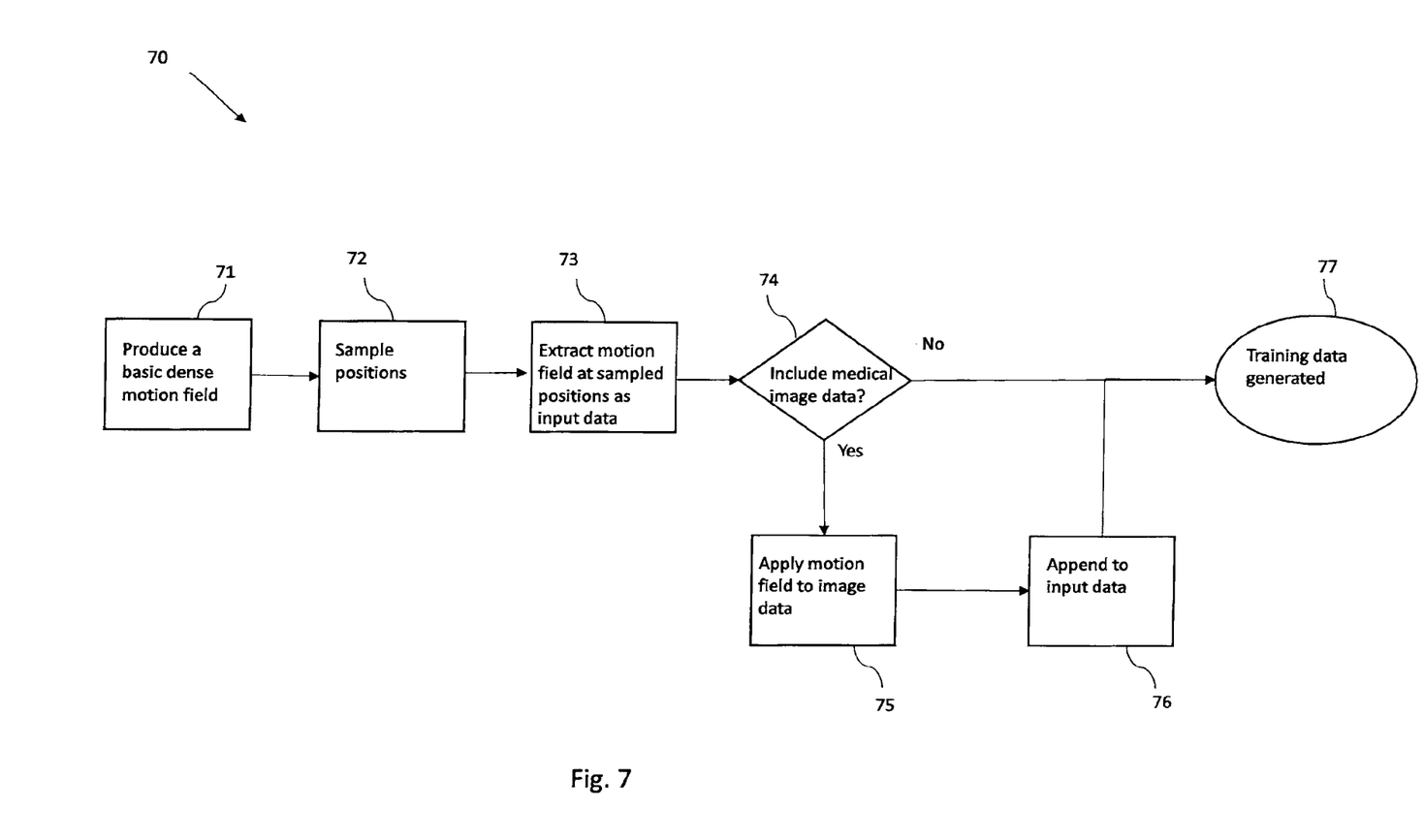
FIG. 7 is a flow chart illustrating an embodiment of the present invention.

FIG. 7 is a flow chart describing the generation of synthetic data. In step 71, a basic or ground dense motion field or displacement field is produced or created describing displacement vectors for a number of points in a data set, each displacement vector specifying a position of a point in reference to a previous position. At step 72, a number of positions are sampled and at step 73, a dense motion field is extracted based on the sampled positions as input data. At step 74, a selection is made whether to include medical image data of a patient into the generation of synthetic data. If yes, the procedure moves to step 75, where the displacement filed is applied to the medical image data and further to step 76 where the result from step 75 is appended to the input data, i.e. the extracted displacement filed at the sampled positions. Then, at step 77, the training data is generated. If no at step 74, the procedure proceeds directly to step 77. Data can be generated and stored in advance, or it can be generated on-the-fly. Mathematical models for motion fields include LDDMM, Gaussian Processes (GP), physical model (e.g. biomechanical model), physics simulation, video game engine. Realistic motion field can be learned via a learned generative model, e.g. GAN, normalizing flow. Motion fields can be "borrowed" from other applications, where data is more plentiful, e.g. 4D CT, ultrasound; further, such motion fields could be artificially distorted to increase the number of examples, using for instance data augmentation methods.

Figure 8:
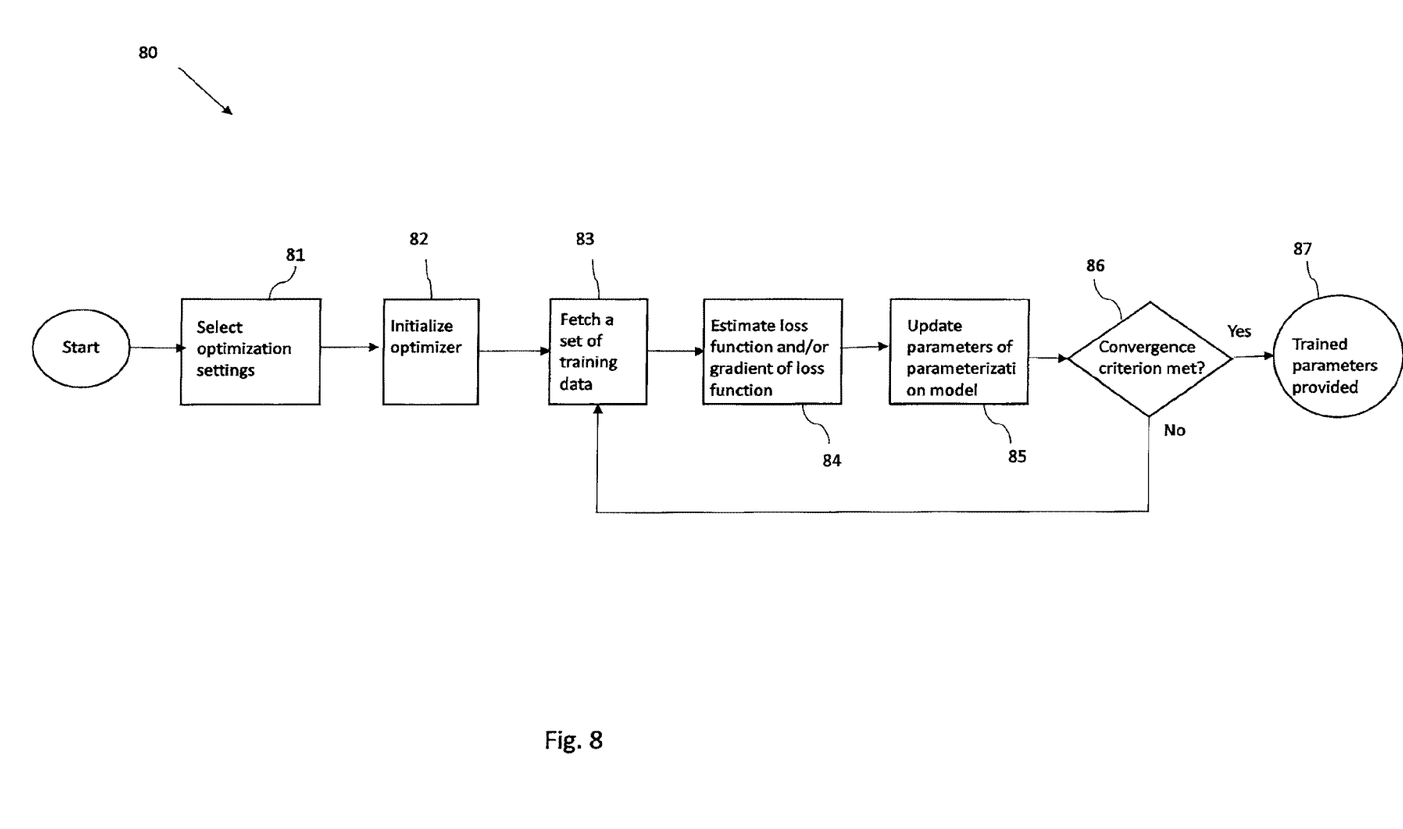
FIG. 8 is a flow chart illustrating an embodiment of the present invention.

Noise could be added to any part of the data generation, including the ground truth motion field, the sampled coordinates, and the confidence With reference to FIG. 8, the training of the machine learning model will be described. First, at step 81, optimization settings are selected which may include choosing an optimizer, for example: a least-squares method; a derivative-free method such as Nelder-Mead, genetic algorithms, Bayesian optimization; a stochastic gradient descent method such as Adam, RMSProp, AdaGrad; conjugate gradient descent; a quasi-Newton method such as BFGS or L-BFGS; a method for constrained optimization such as SQP or an interior point method; a linear programming method such as a simplex method; a global optimization method such as a branch-and-bound method. The step of selecting optimization settings may further include selecting the loss function (objective function), constraints, batch size, learning rate, initial guess, weight initialization and specifying optimizer hyperparameters such as step-length, trust-region size, various tolerances. At step 82, the optimizer is initalized and in step 83, sets of training data is collected. In step 84, the loss function is estimated and/or the gradient of the loss function is estimated based on the training data. In step 85, the parameters of the parameterized model is updated based on the estimated loss function and/or its gradient. At step 86, it is checked whether a convergence criterion is met, e.g. maximum number of iterations reached, maximum number of function evaluations reached, maximum number of epochs reached, duality gap small enough, step size small enough, loss function improvement small enough, norm of gradient small enough, running time long enough If no, the procedure returns to step 83, where further training data may be collected. If yes in step 86, the procedure proceeds to step 87 where trained parameters are provided.

Figure 9:
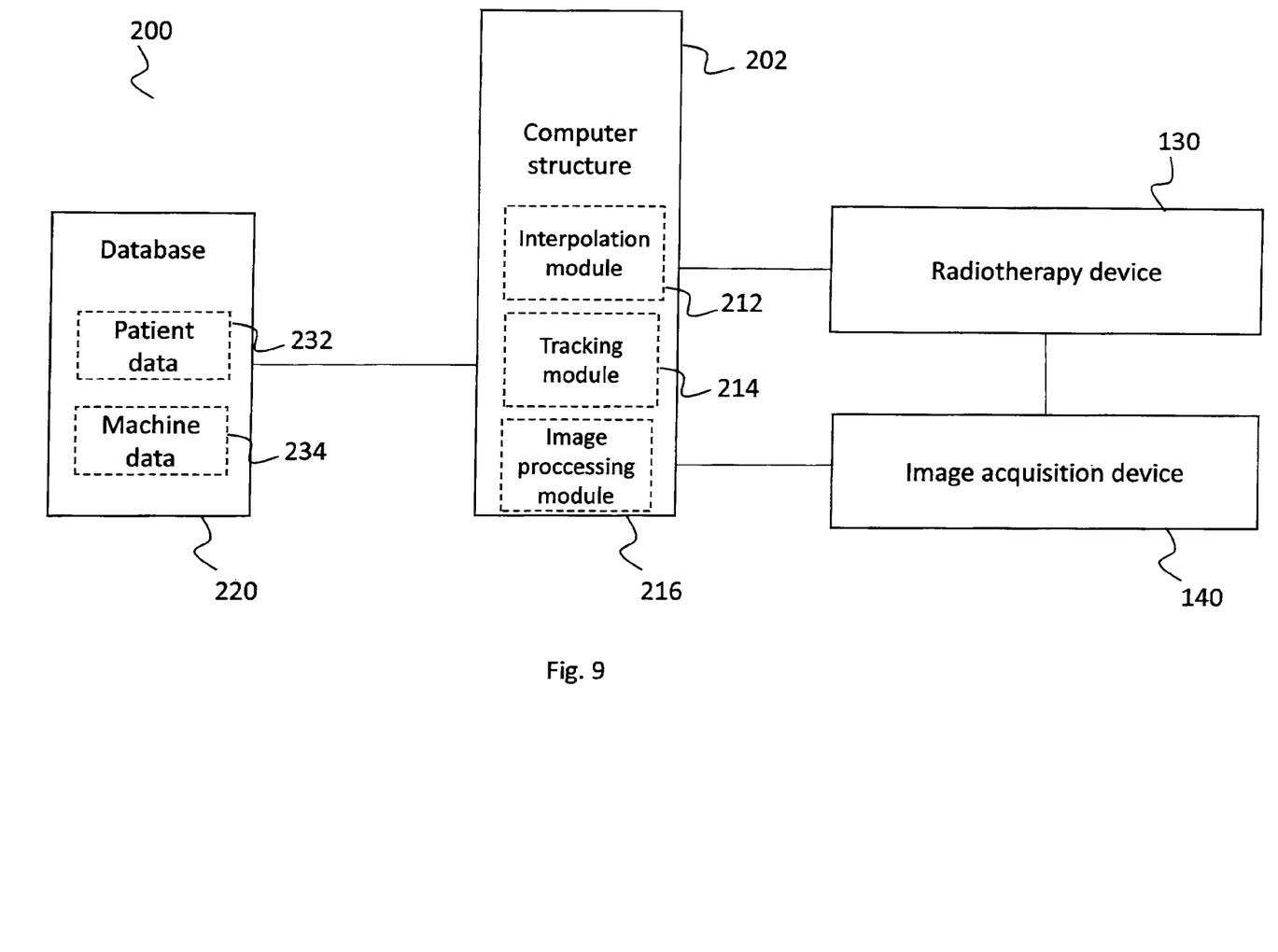
FIG. 9 shows a software structure and system according to embodiments of the present invention.

Turning now to FIG. 9, a computer structure or software 202 in which the methods according to the present invention may be implemented will be described. The computer structure or software 202 may be included in a radiation therapy system 200 as shown in FIG. 9. As shown in FIG. 9, radiation therapy system 200 may include a computer structure 202, a database 220, a radiation therapy device 130 such as a MR linac radiation therapy device, for example, an Elekta Unity® described above with reference to FIG. 1. The computer structure 202 may include hardware and software components to control radiation therapy device 130 including an image acquisition device 140 and/or to perform functions or operations such as treatment planning using a treatment planning software and dose planning using computer structure or software 202, treatment execution, image acquisition, image processing, motion tracking, motion management, or other tasks involved in a radiation therapy process.

The hardware components of computer structure 202 may include one or more computers (e.g., general purpose computers, workstations, servers, terminals, portable/mobile devices, etc.); processor devices (e.g., central processing units (CPUs), graphics processing units (GPUs), microprocessors, digital signal processors (DSPs), field programmable gate arrays (FPGAs), special-purpose or specially-designed processors, etc.); memory/storage devices (e.g., read-only memories (ROMs), random access memories (RAMs), flash memories, hard drives, optical disks, solid-state drives (SSDs), etc.); input devices (e.g., keyboards, mice, touch screens, mics, buttons, knobs, trackballs, levers, handles, joysticks, etc.); output devices (e.g., displays, printers, speakers, vibration devices, etc.); or other suitable hardware. The software components of computer structure 202 may include operation system software, application software, etc. For example, as shown in FIG. 9, computer structure 202 includes an image processing module 216, for example, executing pre-processing of image data, a tracking module 214 including for example, the feature extractor, and an interpolation module 212 including a deep learning module performing normalized convolutions as described above.

Software 212, 214 and 216 may include computer readable and executable codes or instructions for performing the processes described in detail in this application. For example, a processor device of computer structure 202 may be communicatively connected to a memory/storage device storing software 212, 214, and 216 to access and execute the codes or instructions. The execution of the codes or instructions may cause the processor device to perform operations to achieve one or more functions consistent with the disclosed embodiments.

The software 221, 214, and 216 be configured to execute the methods described herein, for example, the methods described with reference to FIGS. 2-8.

Further, computer structure 202 may be communicatively connected to a database 220 to access data. In some embodiments, database 220 may be implemented using local hardware devices, such as one or more hard drives, optical disks, and/or servers that are in the proximity of computer structure 202. In some embodiments, database 220 may be implemented in a data center or a server located remotely with respect to computer structure 202. Computer structure 202 may access data stored in database 220 through wired or wireless communication.

Database 220 may include patient data 232. Patient data may include information such as (1) imaging data associated with a patient anatomical region, organ, or volume of interest segmentation data (e.g., MRI, CT, X-ray, PET, SPECT, and the like); (2) functional organ modeling data (e.g., serial versus parallel organs, and appropriate dose response models); (3) radiation dosage data (e.g., may include dose-volume histogram (DVH) information); or (4) other clinical information about the patient or course of treatment.

Database 220 may include machine data 224. Machine data 224 may include information associated with radiation therapy device 130, image acquisition device 140, or other machines relevant to radiation therapy, such as radiation beam size, arc placement, on/off time duration, radiation treatment plan data, multi-leaf collimator (MLC) configuration, MRI pulse sequence, and the like.

Image acquisition device 140 may provide medical images of a patient. For example, image acquisition device 140 may provide one or more of MRI images (e.g., 2D MRI, 3D MRI, 2D streaming MRI, 4D volumetric MRI, 4D cine MRI); Computed Tomography (CT) images; Cone-Beam CT images; Positron Emission Tomography (PET) images; functional MRI images (e.g., fMRI, DCE-MRI, diffusion MRI); X-ray images; fluoroscopic images; ultrasound images; radiotherapy portal images; Single-Photo Emission Computed Tomography (SPECT) images; and the like. Accordingly, image acquisition device 140 may include an MRI imaging device, a CT imaging device, a PET imaging device, an ultrasound imaging device, a fluoroscopic device, a SPECT imaging device, or other medical imaging devices for obtaining the medical images of the patient.

Various operations or functions are described herein, which may be implemented or defined as software code or instructions. Such content may be directly executable ("object" or "executable" form), source code, or difference code ("delta" or "patch" code). Software implementations of the embodiments described herein may be provided via an article of manufacture with the code or instructions stored thereon, or via a method of operating a communication interface to send data via the communication interface. A machine or computer readable storage medium may cause a machine to perform the functions or operations described, and includes any mechanism that stores information in a form accessible by a machine (e.g., computing device, electronic system, and the like), such as recordable/non-recordable media (e.g., read only memory (ROM), random access memory (RAM), magnetic disk storage media, optical storage media, flash memory devices, and the like). A communication interface includes any mechanism that interfaces to any of a hardwired, wireless, optical, and the like, medium to communicate to another device, such as a memory bus interface, a processor bus interface, an Internet connection, a disk controller, and the like. The communication interface can be configured by providing configuration parameters and/or sending signals to prepare the communication interface to provide a data signal describing the software content. The communication interface can be accessed via one or more commands or signals sent to the communication interface.

The present disclosure also relates to a system for performing the operations herein. This system may be specially constructed for the required purposes, or it may comprise a general-purpose computer selectively activated or reconfigured by a computer program stored in the computer. Such a computer program may be stored in a computer readable storage medium, such as, but not limited to, any type of disk including floppy disks, optical disks, CDROMs, and magnetic-optical disks, read-only memories (ROMs), random access memories (RAMs), EPROMS, EEPROMs, magnetic or optical cards, or any type of media suitable for storing electronic instructions, each coupled to a computer system bus.

The order of execution or performance of the operations in embodiments of the present disclosure illustrated and described herein is not essential, unless otherwise specified. That is, the operations may be performed in any order, unless otherwise specified, and embodiments of the present disclosure may include additional or fewer operations than those disclosed herein. For example, it is contemplated that executing or performing a particular operation before, contemporaneously with, or after another operation is within the scope of aspects of the present disclosure.

Embodiments of the present disclosure may be implemented with computer-executable instructions. The computer-executable instructions may be organized into one or more computer-executable components or modules. Aspects of the present disclosure may be implemented with any number and organization of such components or modules. For example, aspects of the present disclosure are not limited to the specific computer-executable instructions or the specific components or modules illustrated in the figures and described herein. Other embodiments of the present disclosure may include different computer-executable instructions or components having more or less functionality than illustrated and described herein.

When introducing elements of aspects of the present disclosure or the embodiments thereof, the articles "a," "an," "the," and "said" are intended to mean that there are one or more of the elements. The terms "comprising," "including," and "having" are intended to be inclusive and mean that there may be additional elements other than the listed elements.

Having described aspects of the present disclosure in detail, it will be apparent that modifications and variations are possible without departing from the scope of aspects of the present disclosure as defined in the appended claims. As various changes could be made in the above constructions, products, and methods without departing from the scope of aspects of the present disclosure, it is intended that all matter contained in the above description and shown in the accompanying drawings shall be interpreted as illustrative and not in a limiting sense.

The invention claimed is:

1. A method for image registration of images of a patient comprising:
receiving a first set of image data from the patient;
selecting one or more tracking regions in said first set of image data, each tracking region including multiple tracking targets;
receiving multiple sets of image data, each of the multiple sets of image data captured at different times from the patient;
identifying corresponding tracking targets in said multiple sets of image data captured at different times;
creating a sparse motion field describing motion vectors of the multiple tracking targets, the motion vectors specifying a position of a tracking target in reference to a previous position of the tracking target;
estimating a displacement field describing displacement vectors for a number of points in each respective set of said multiple sets of image data, the points located within said one or more tracking regions, and each displacement vector specifying a position of a point in the respective set of image data in reference to a previous position of the same point in another set of the image data captured at a previous time, wherein estimating the displacement field includes using sparse-to-dense interpolation of the sparse motion field to produce the displacement field; and
creating a representation of at least one image based on said displacement field.

2. The method according to claim 1, wherein selecting the one or more tracking regions comprises:
performing a feature extraction, wherein said one or more tracking regions are selected based on the feature extraction.

3. The method according to claim 1, wherein selecting the one or more tracking regions comprises:
adding or removing at least one tracking region as a response to a performance of the selected one or more tracking regions and/or as an update of a feature extraction.

4. The method according to claim 1, further comprising:
determining whether said selected one or more tracking regions deliver a satisfying performance;
if it is determined that the performance is satisfactory, terminating the selection of the one or more tracking regions;
if it is determined that the performance is not satisfactory, adding or removing tracking targets in the one or more tracking regions.

5. The method according to claim 1, wherein identifying the corresponding tracking targets in said multiple sets of image data, further comprises:
identifying corresponding potential tracking targets using a feature extracting model;
identifying matching candidates for said potential tracking targets; and
using said matching candidates for said potential tracking targets to estimate the displacement field.

6. The method according to claim 5, wherein identifying the corresponding tracking targets in said multiple sets of image data, further comprises:
using identified tracking targets for updating said feature extracting model.

7. The method according to claim 1, wherein estimating the displacement field further comprises using image data from said multiple sets of image data in said sparse-to-dense interpolation.

8. The method according to claim 1, wherein estimating the displacement field further comprises using a machine learning model to produce the displacement field, wherein said sparse motion field is used as input to the machine learning model.

9. The method according to claim 8, wherein said machine learning model uses normalized convolutions.

10. The method according to claim 8, wherein said machine learning model is a neural network.

11. The method according to claim 1, wherein creating the representation of the at least one image is further based on the sparse motion field describing the motion vectors of the multiple tracking targets.

12. A method for training a machine learning model to be used in image registration of images of a patient comprising:
creating one or more displacement fields describing displacement vectors for a number of points in each respective set of multiple sets of image data, wherein each of the multiple sets of image data are captured at different times, and wherein each displacement vector specifies a position of a point in the respective set of image data in reference to a previous position of the same point in another set of the image data captured at a previous time;
sampling a number of positions associated with corresponding displacement vectors;
extracting the one or more displacement fields at sampled positions as input training data to the machine learning model;
estimating a loss function and/or its gradient for said machine learning model using the input training data; and
updating parameters of a parameterized model of said machine learning model based on the estimated loss function and/or its gradient;
wherein said machine learning model is trained to estimate a displacement field from a new set of image data, and create a representation of at least one image of the new set of image data based on the estimated displacement field, wherein said machine learning model is configured to produce the displacement field using sparse-to-dense interpolation of a sparse motion field that describes motion vectors of multiple tracking targets.

13. The method according to claim 12, further comprising:
specifying the parameterized model of the machine learning model; and
specifying the loss function of the machine learning model.

14. The method according to claim 12, further comprising:
generating synthetic image data to the machine learning model for use as training data.

15. The method according to claim 12, further comprising:
gathering image data of a patient;
applying said one or more displacement fields to the image data to create a resulting displacement field; and
modifying said input training data based on the resulting displacement field.

16. The method according to claim 12, further comprising:
gathering further training data to the machine learning model if a convergence criterion has not been met, estimating the loss function and/or its gradient of said machine learning model using the further training data; and updating the parameters of the parameterized model of said machine learning model based on the estimated loss function and/or its gradient.

17. A non-transitory computer-readable medium having stored therein computer-readable instructions for a processor, wherein the instructions when read and implemented by the processor, cause the processor to:

select one or more tracking regions in a first set of image data of an image of a patient, each tracking region including multiple tracking targets;

identify corresponding tracking targets in multiple sets of image data from multiple images captured at different times from the patient;

create a sparse motion field describing motion vectors of the multiple tracking targets, the motion vectors specifying a position of a tracking target in reference to a previous position of the tracking target;

estimate a displacement field describing displacement vectors for a number of points in each respective set of said multiple sets of image data, the points located within said one or more tracking regions, and each displacement vector specifying a position of a point in the respective set of image data in reference to a previous position of the same point in another set of the image data captured at a previous time, wherein to estimate the displacement field includes use of sparse-to-dense interpolation of the sparse motion field to produce the displacement field; and create a representation of at least one image based on said displacement field.

18. The non-transitory computer-readable medium according to claim 17, wherein to create the representation of the at least one image is further based on the sparse motion field describing the motion vectors of the multiple tracking targets.

* * * * *